(12) United States Patent
Reddy et al.

(10) Patent No.: US 7,122,571 B2
(45) Date of Patent: Oct. 17, 2006

(54) SUBSTITUTED HYDRAZONES AS INHIBITORS OF CYCLOOXYGENASE-2

(75) Inventors: E. Premkumar Reddy, Villanova, PA (US); M.V. Ramana Reddy, Upper Darby, PA (US)

(73) Assignee: Temple University - Of The Commonwealth System of Higher Education, Philadelphia, PA (US)

( * ) Notice: Subject to any disclaimer, the term of this patent is extended or adjusted under 35 U.S.C. 154(b) by 383 days.

(21) Appl. No.: 10/315,494

(22) Filed: Dec. 10, 2002

(65) Prior Publication Data

US 2003/0187035 A1    Oct. 2, 2003

Related U.S. Application Data

(60) Provisional application No. 60/338,927, filed on Dec. 10, 2001.

(51) Int. Cl.
A61K 31/405 (2006.01)
A61K 31/38 (2006.01)
A61K 31/34 (2006.01)
A61K 31/18 (2006.01)
C07D 209/14 (2006.01)
C07D 333/20 (2006.01)
C07C 323/00 (2006.01)

(52) U.S. Cl. ............... 514/415; 514/438; 514/471; 514/602; 514/603; 548/503; 549/74; 549/492; 564/85; 564/86

(58) Field of Classification Search ............ 564/86, 564/251
See application file for complete search history.

(56) References Cited

U.S. PATENT DOCUMENTS

| 3,629,241 A | * | 12/1971 | Krause et al. | 548/379.4 |
| 4,656,184 A | | 4/1987 | Coquelet et al. | 514/370 |
| 4,732,904 A | | 3/1988 | Morgan et al. | 514/357 |
| 5,072,042 A | | 12/1991 | Janssen et al. | 564/251 |
| 5,665,883 A | | 9/1997 | Baker et al. | 546/210 |

FOREIGN PATENT DOCUMENTS

| FR | 69 22269 | 3/1970 |
| GB | 2297089 A | 7/1996 |
| WO | 84/00007 A | 1/1984 |

OTHER PUBLICATIONS

Saduikis et al, Chemija, Synthesis of Substituted Arylsulfonylarylideneimines, Arylsulfonylhydrazones, and Arylhydrazones, 1993, vol. date 1992, (3), pp. 120-130. English Translation.*

Shyam et al, Journal of Medicinal Chemistry 1985, 28 pp. 149-152.*

Lespagnol et al, Bulletin de la Societe Chimique de France 1963, pp. 46-50.*

Synthesis of Substituted Arylsulfonylarylidenimines, Arylsulfonylhydrazones, and Arylhydrazones. Saduikis, G.; Kazlauskas, D. Inst. Khim. Vilnius, Vilnius, Lithuania. Chemija (1993), vol. Date 1992, (3), 120-30. ISSN: 0235-7216.

Exploratory Laboratory Catalog, Ambinter Company, Paris, France, Updated in electronic database, Jan. 21, 2002, Catalog entry for "benzenesulfonamide, 4[[(4-methoxyphenyl)methylene]hydrazino]-," CA registration No. 381692-57-5.

Krishnamurthy Shyam et al., "Relationship between structure and antineoplastic activity of (arylsulfonyl) hydrazones of 4-pyridinecarboxaldehyde", Journal of Medicinal Chemistry, vol. 28, 1985, pp. 149-152.

Jesse A. May et al., "Antineoplastic properties of arylsulfonylhydrazones of 3-formylpyridazine 2-oxide and 4-formylpyrimidine 3-oxide", Journal of Medicinal Chemistry, vol. 21, No. 12, 1978, pp. 1333-1335.

Patent Abstracts of Japan, vol. 004, No. 081 (C-014), Jun. 11, 1980 abstracting JP 55 045657 A.

* cited by examiner

*Primary Examiner*—Paul A. Zucker
(74) *Attorney, Agent, or Firm*—Drinker Biddle & Reath LLP; Daniel A. Monaco

(57) ABSTRACT

Compounds useful as inhibitors of cyclooxygenase-2 activity have the formulae I or Ia:

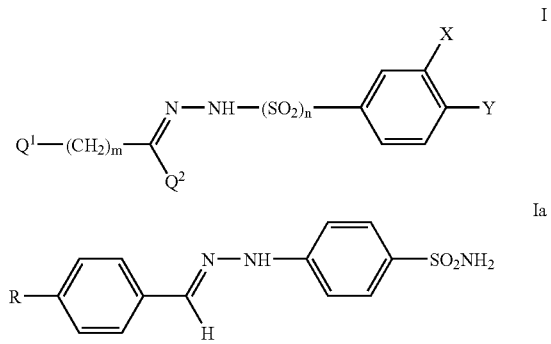

wherein: $Q^1$, $Q^2$, n, m, X, Y and R are as defined herein.

44 Claims, 3 Drawing Sheets

SUBSTITUTED HYDRAZONES AS INHIBITORS OF CYCLOOXYGENASE-2

CROSS-REFERENCE TO RELATED APPLICATIONS

The benefit of the filing date of U.S. Provisional patent application Ser. No. 60/338,927, filed Dec. 10, 2001, is hereby claimed pursuant to 35 U.S.C. 119(e). The entire disclosure of the aforesaid provisional application is incorporated herein by reference.

FIELD OF THE INVENTION

The invention relates generally to anti-inflammatory drugs, and more particularly to novel compounds which inhibit the activity of cyclooxygenase-2.

BACKGROUND OF THE INVENTION

The metabolites of arachidonic acid, such as prostaglandins, lipoxygenases and thromboxane products are produced in a wide variety of tissues and play a key role in several biological responses. Prostaglandins mediate both beneficial and undesirable biological reactions. The production of prostaglandins induces pain, swelling, heat and redness which are characteristic features of inflammation. The chronic inflammation associated with prostaglandin production leads to the breakdown of the injured tissue and angiogenesis. In pathologic chronic inflammation, normal tissues can be destroyed and the new blood vessel formation can support growth of abnormal tissue. Prostaglandins are also important for normal physiological processes in different organs. In the stomach, prostaglandins protect mucosa from acid. They also regulate blood flow and salt-water balance in the kidney. Prostaglandins are also important in platelet aggregation and participate in memory and other cognitive functions.

Prostaglandins are produced from cell membrane phospholipids by a cascade of enzymes. The enzymatic activities involve release of arachidonic acid from the cell membrane by phospholipase $A_2$, followed by the conversion of arachidonic acid to a common prostaglandin precursor, $PGH_2$, by cyclooxygenase (also called prostaglandin H synthase). $PGH_2$ is finally converted to various types of prostaglandins ($PGE_1$, $PGE_2$, $PGI_2$ or prostacyclin, $PGF_{2\alpha}$ and thromboxane) by cell-specific synthases.

Aspirin and other nonsteroidal anti-inflammatory drugs (NSAID's) block the formation of prostaglandins by inhibiting cyclooxygenase activity. They have analgesic, antipyretic and anti-inflammatory activities. However, chronic treatment with the available NSAID's often leads to disruption of beneficial prostaglandin-mediated processes. The side effects associated with constant usage of NSAID's include gastrointestinal (GI) irritation and formation of life-threatening GI ulcers.

A dramatic advance in the field of inflammation research came with discovery of multiple enzymes for each step of the prostaglandin synthase cascade. The research suggested that in some situations, such as inflammation, cyclooxygenase was inducible. The cyclooxygenase known at the time, cyclooxygenase-1 (COX-1), was clearly non-inducible or modulated by glucocorticoids. A second, inducible form of cyclooxygenase known as cyclooxygenase-2 (COX-2) was subsequently identified and cloned by several groups of investigators. COX-1 is the constitutive cyclooxygenase isoform and is mainly responsible for the synthesis of cytoprotective prostaglandins in the GI tract and the synthesis of thromboxane which triggers platelet aggregation in blood platelets. COX-2 is inducible and short lived except in the case of certain tumors where it is constitutively activated. COX-2 expression is stimulated in response to endotoxins, cytokines, hormones, growth factors and mitogens. These observations suggest that COX-1 and COX-2 serve different physiological and pathophysiological functions. Indeed, it has been suggested that COX-1 is responsible for endogenous basal release of prostaglandins and hence is important to the physiological functions of prostaglandins such as GI integrity and renal blood flow. On the other hand, it has been suggested that COX-2 is mainly responsible for the pathological effects of prostaglandins, where induction of the enzyme occurs in response to inflammatory agents, hormones, growth factors and cytokines. See, U.S. Pat. No. 5,604,253, incorporated herein by reference, for a discussion of the advantages of selective COX-2 inhibition. Principally, a selective COX-2 inhibitor is expected to possess similar anti-inflammatory, antipyretic and analgesic properties to a conventional NSAID but with reduced potential for gastrointestinal toxicity, and a reduced potential for renal side effects.

The differential tissue distribution of COX-1 and COX-2 provides an approach to develop selective inhibitors for COX-2 with reduced effect on COX-1, thereby preventing gastric side effects.

A number of selective COX-2 inhibitors have been reported. These include diaryl heterocyclics (Penning et al., *J. Med. Chem*, 40, 1347–1365 (1997); acetoxyphenyl alkyl sulfides (Kalgutkar et al., *J. Med. Chem*, 41, 4800–4818 (1998); methane sulfonanilides (Li et al., *J. Med. Chem*, 38, 4897–4905 (1995); and tricyclic inhibitor classes (Wilkerson et al., *J. Med. Chem.*, 38, 3895–3901 (1995). U.S. Pat. No. 5,604,253 discloses N-benzylindol-3-yl propanoic acid derivatives as cyclooxygenase inhibitors.

What are needed are additional COX-2 inhibitors, particularly compounds which selectively inhibit the cyclooxygenase activity of COX-2 over COX-1.

SUMMARY OF THE INVENTION

Compounds and pharmaceutical compositions thereof are provided for inhibiting the biological activity of COX-2, in particular the cyclooxygenase activity of COX-2. Methods of treating disease conditions which are associated with undesired prostaglandin production and/or secretion are also provided, as well as treatment of cyclooxygenase-mediated disorders. Methods for synthesizing compounds of the invention and intermediates thereof are also provided.

In one embodiment of the invention, there is provided a pharmaceutical composition of one or more compounds of formula I, or a pharmaceutically acceptable salt thereof, in combination with a pharmaceutically effective carrier,

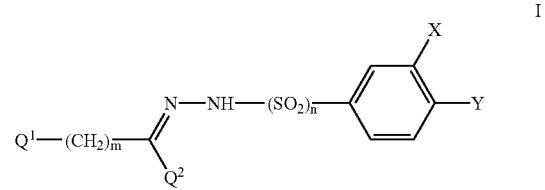

wherein:

Q¹ is selected from the group consisting of hydrogen, trifluoromethyl, (C₁–C₈)alkyl, substituted and unsubstituted aryl, and substituted and unsubstituted heteroaryl;

Q² is selected from the group consisting of hydrogen, trifluoromethyl, (C₁–C₈)alkyl, substituted and unsubstituted aryl, substituted and unsubstituted heteroaryl, substituted and unsubstituted aryl(C₁–C₃)alkyl, substituted and unsubstituted heteroaryl(C₁–C₃)alkyl;

n is zero or one;

m is zero, one, two or three;

X is selected from the group consisting of hydrogen and hydroxymethyl; and

Y is selected from the group consisting of hydrogen, (C₁–C₈)alkyl, (C₁–C₈)alkoxy, nitro, amino, sulfamyl and (C₁–C₃)alkylsulfonyl;

provided:
(i) Q¹ and Q² may not both be hydrogen in the same compound;
(ii) Q¹ and Q² may not both be (C₁–C₈)alkyl in the same compound;
(iii) when n is zero, Y must be sulfamyl or (C₁–C₃)alkylsulfonyl;
(iv) when m and n are both zero and Q² is —H or (C₁–C₈)alkyl, then Q¹ may not be phenyl, unless substituted at the 4-position by other than hydroxy, alkyl, alkoxy or alkoxyalkyl; and
(v) when n is one, Q² must be trifluoromethyl.

In another embodiment of the invention, novel compounds and pharmaceutically acceptable salts thereof, are provided. The novel compounds have the of formula I, wherein Q¹, Q², m, n, X and Y are defined as above;

provided:
(i) Q¹ and Q² may not both be hydrogen in the same compound;
(ii) Q¹ and Q² may not both be (C₁–C₈)alkyl in the same compound;
(iii) when n is zero, Y must be sulfamyl or (C₁–C₃)alkylsulfonyl;
(iv) when m and n are both zero and Q² is —H or (C₁–C₈)alkyl, then Q¹ may not be phenyl, unless substituted at the 4-position by other than chlorine, bromine, hydroxy, alkyl, alkoxy or alkoxyalkyl; and
(v) when n is one, Q² must be trifluoromethyl.

According to one embodiment of novel compounds according to formula I, when n and m are both zero and Q² is —H or —(C₁–C₈)alkyl, Q¹ is not phenyl, unless substituted at the 4-position by other than halogen, hydroxy, alkyl, alkoxy or alkoxyalkyl.

In one embodiment of the compounds of formula I, at least one of Q¹ and Q² is selected from the group consisting of substituted and unsubstituted aryl, and substituted and unsubstituted heteroaryl.

The substituents for the substituted aryl, aryl(C₁–C₃)alkyl, heteroaryl and heteroaryl(C₁–C₃)alkyl groups comprising Q¹ and Q² are preferably independently selected from the group consisting of halogen, (C₁–C₈)alkyl, (C₁–C₈)alkoxy, nitro, cyano, carboxy, carboxy(C₁–C₃)alkoxy, hydroxy, (C₂–C₆)hydroxyalkyl, phosphonato, amino, (C₁–C₈)acylamino, sulfamyl, acetoxy, di(C₁–C₆)alkylamino(C₂–C₆ alkoxy), trifluoromethyl and

wherein:

Z is oxygen or sulfur,

R¹ is selected from the group consisting of hydrogen, (C₁–C₈)alkyl, (C₂–C₈)heteroalkyl, substituted phenyl and unsubstituted phenyl; and R² is selected from the group consisting of hydrogen, (C₁–C₈)alkyl, (C₂–C₈)heteroalkyl, substituted aryl, unsubstituted aryl, substituted heteroaryl, unsubstituted heteroaryl, substituted aryl(C₁–C₃)alkyl, unsubstituted aryl(C₁–C₃)alkyl and (C₁–C₆)alkoxycarbonyl(C₁–C₆)alkylenyl; and wherein the substituents for the substituted aryl and substituted heteroaryl groups comprising or included within R¹ and R², are independently selected from the group consisting of halogen, (C₁–C₈)alkyl, (C₁–C₈)alkoxy, nitro, cyano, carboxy, carboxy(C₁–C₃)alkoxy, hydroxy, (C₂–C₆)hydroxyalkyl, phosphonato, amino, (C₁–C₈)acylamino, sulfamyl, acetoxy, di(C₁–C₆)alkylamino(C₂–C₆ alkoxy) and trifluoromethyl.

According to one principal embodiment of the compounds of formula I, n is zero, and Y is sulfamyl or (C₁–C₃)alkylsulfonyl. According to a preferred embodiment of such compounds, Q² is selected from the group consisting of hydrogen, (C₁–C₈)alkyl and trifluoromethyl. In other embodiments, X is preferably hydrogen. In some embodiments Q¹ is substituted or unsubstituted heteroaryl. In yet other embodiments, Q¹ is substituted or unsubstituted phenyl, particularly substituted phenyl wherein the phenyl moiety is substituted with halogen, (C₁–C₈)alkyl, (C₁–C₈)alkoxy or a combination thereof. In some embodiments, m is zero and Q² is hydrogen.

While the substituents on the ring system of Q¹ in formula I, particularly when Q¹ is phenyl, may be placed at any point on the ring, substitution in at least the 4-position is particularly preferred, particularly 2,4-disubstitution and 4-monosubstitution. Preferred substituents at the 4-position include the substituents for Q¹ and Q² provided above. When m and n are zero and Q² is hydrogen or alkyl, Q¹ in formula I is preferably substituted at the 4-position by carboxy(C₁–C₃)alkoxy, hydroxy(C₂–C₆)alkyl, phosphonato, amino, (C₁–C₈)acylamino, sulfamyl, acetoxy, di(C₁–C₆)alkylamino(C₂–C₆)alkoxy, trifluoromethyl and

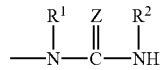

wherein, R¹, R² and Z are defined as above. Halogen is particularly preferred as a 4-position substituent in compounds of the invention for pharmaceutical use.

According to another principal embodiment of the invention, m is one, and Q² is trifluoromethyl. According to a preferred embodiment of such compounds, Y is selected from the group consisting of hydrogen, (C₁–C₈)alkyl, sulfamyl and (C₁–C₃)alkylsulfonyl. According to a more preferred embodiment, such compounds include benzyl trifluoromethylketone-4-sulfamylphenylhydrazone and benzyl trifluoromethylketone toluenesulfonyl-hydrazone.

In a related aspect, the invention is directed to a pharmaceutical composition of one or more compounds of formula Ia, or a pharmaceutically acceptable salt thereof, in combination with a pharmaceutically effective carrier.

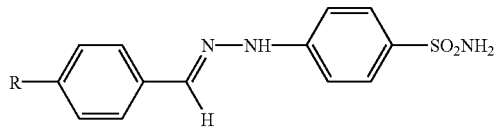

Ia wherein R is selected from halogen, $(C_1-C_8)$alkyl and $(C_1-C_8)$alkoxy; preferably $(C_1-C_3)$alkyl and $(C_1-C_3)$alkoxy; most preferably methyl and methoxy.

Exemplary compounds of formula Ia, for pharmaceutical use, include, for example, include 4-methylbenzaldehyde-4-sulfamylphenylhydrazone, 4-fluorobenzaldehyde-4-sulfamylphenylhydrazone, 4-chlorobenzaldehyde-4-sulfamylphenylhydrazone, 4-bromobenzaldehyde-4-sulfamylphenylhydrazone, 4-methoxybenzaldehyde-4-sulfamylphenyl-hydrazone, and pharmaceutically acceptable salts thereof.

In a related aspect, the invention is directed to novel compounds of formula Ia, and pharmaceutically acceptable salts thereof,

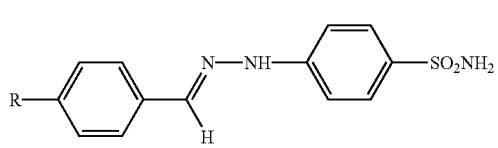

Ia wherein R is selected from fluorine, $(C_1-C_8)$alkyl and $(C_2-C_8)$alkoxy. R is preferably selected from $(C_1-C_3)$alkyl and $(C_2-C_3)$alkoxy, most preferably methyl and ethoxy.

Exemplary novel compounds of formula Ia, include, for example, include 4-methylbenzaldehyde-4-sulfamylphenylhydrazone and 4-fluorobenzaldehyde-4-sulfamylphenylhydrazone, and pharmaceutically acceptable salts thereof.

According to yet another embodiment of the invention, a method for treating a cyclooxygenase-mediated disease is provided comprising administering an effective amount of a pharmaceutical composition of a compound according to formulae I or Ia, as such composition is defined above, to an animal in need of such treatment. The expression "animal" is inclusive of human beings.

According to yet another embodiment of the invention, a process for preparing compounds of formula I is provided. The process comprises reacting a compound of formula II,

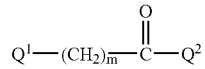

II with a compound of formula III,

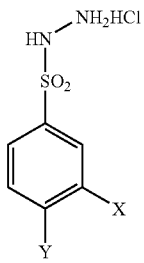

III and obtaining a compound of formula I, wherein $Q^1$, $Q^2$, n, m, X and Y are defined as above, or a pharmaceutically acceptable salt thereof;

provided:
(i) $Q^1$ and $Q^2$ may not both be hydrogen in the same compound;
(ii) $Q^1$ and $Q^2$ may not both be $(C_1-C_8)$alkyl in the same compound;
(iii) when n is zero, Y must be sulfamyl or $(C_1-C_3)$alkylsulfonyl;
(iv) when m and n are both zero and $Q^2$ is —H or $(C_1-C_8)$alkyl, then $Q^1$ may not be phenyl, unless substituted at the 4-position by other than chlorine, bromine, hydroxy, alkyl, alkoxy or alkoxyalkyl; and
(v) when n is one, $Q^2$ must be trifluoromethyl.

According to yet another embodiment of the invention, a process for preparing compounds of formula Ia is provided.

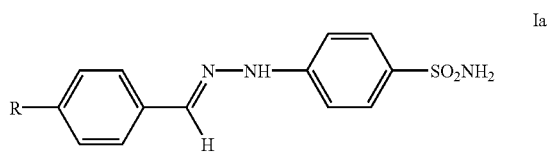

Ia wherein R is selected from fluorine, $(C_1-C_8)$alkyl and $(C_2-C_8)$alkoxy. R is preferably selected from $(C_1-C_3)$alkyl and $(C_2-C_3)$alkoxy, most preferably methyl and ethoxy.

The process comprises reacting a compound of formula IIa;

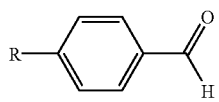

IIa with a compound of formula IIIa,

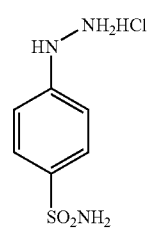

IIIa and obtaining a compound according to formula Ia, or a pharmaceutically acceptable salt thereof.

The term "$(C_2-C_8)$acylamino" means a radical containing a two to eight carbon straight or branched chain acyl group attached to a nitrogen atom via the acyl carbonyl carbon. Examples include —NHC(O)CH$_2$CH$_2$CH$_3$ and —NHC(O)CH$_2$CH$_2$ CH$_2$CH$_2$CH$_3$.

The term "alkyl", by itself or as part of another substituent means, unless otherwise stated, a straight or branched chain hydrocarbon radical, including di- and multi-radicals, having the number of carbon atoms designated (i.e. $C_1-C_8$ means one to eight carbons) and includes straight or branched chain groups. Most preferred is $(C_1-C_6)$alkyl, more preferably $(C_1-C_3)$alkyl, most preferably ethyl or methyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy and the higher homologs and isomers. Preferred are $(C_1-C_6)$alkoxy, more preferably $(C_1-C_3)$ alkoxy, most preferably ethoxy or methoxy.

The term "alkylenyl" by itself or as part of another substituent means a divalent radical derived from a straight or branched chain alkane having the indicated number of carbon atoms, as exemplified by the four-carbon radical —CH$_2$CH$_2$CH$_2$CH$_2$—.

The term "alkenyl" employed alone or in combination with other terms, means, unless otherwise stated, a stable straight chain or branched monounsaturated or diunsaturated hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A divalent radical derived from an alkene is exemplified by —CH=CH—CH$_2$—.

The term "carboxy($C_1-C_3$)alkoxy" means a radical in which the carboxy group —COOH is attached to a carbon of a straight or branched chain alkoxy group containing one, two or three carbon atoms. The radical thus contains up to four carbon atoms. Examples include HOC(O)CH$_2$CH$_2$CH$_2$O— and HOC(O)CH$_2$CH$_2$O—.

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$—S(O)—CH$_3$. Up to two heteroatoms may be consecutive, such as, for example, —CH$_2$—NH—OCH$_3$.

The term "heteroalkenyl" by itself or in combination with another term means, unless otherwise stated, a stable straight or branched chain monounsaturated or diunsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

The term "hydroxyalkyl" means an alkyl radical wherein one or more of the carbon atoms is substituted with hydroxy. Examples include —CH$_2$CH(OH)CH$_3$ and —CH$_2$OH.

The terms "halo" or "halogen" by themselves or as part of another substituent mean, unless otherwise stated, a fluorine, chlorine, bromine, or iodine atom.

The term "$(C_1-C_6)$alkoxycarbonyl$(C_1-C_6)$alkylenyl" means a group of the formula CH$_3$(CH$_2$)$_p$OC(O)(CH$_2$)$_q$— wherein p is an integer from zero to five and q is an integer from one to six.

The term "di$(C_1-C_6)$alkylamino$(C_2-C_6)$alkoxy" means (alkyl)$_2$N(CH$_2$)$_n$O— wherein the two alkyl chains connected to the nitrogen atom independently contain from one to six carbon atoms, preferably from one to three carbon atoms, and n is an integer from 2 to 6. Preferably, n is 2 or 3. Most preferably, n is 2, and the alkyl groups are methyl, that is, the group is the dimethylaminoethoxy group, (CH$_3$)$_2$NCH$_2$CH$_2$O—.

The term "hydroxymethyl" means the group —CH$_2$OH.

The term "phosphonato" means the group —PO(OH)$_2$.

The term "$(C_1-C_3)$alkylsulfonyl" means a radical in which the sulfonyl group, —SO$_2$—, is attached to a carbon atom of a straight or branched chain alkyl group containing one, two or three carbon atoms. Examples include the methanesulfonyl group, (—SO$_2$CH$_3$), which is preferred.

The term "sulfamyl" means, unless otherwise stated, the N-unsubstituted group —SO$_2$NH$_2$.

The term "aromatic" refers to a carbocycle or heterocycle having one or more polyunsaturated rings having aromatic character ((4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner or may be fused. Examples include phenyl; anthracyl; and naphthyl, particularly 1-naphthyl and 2-naphthyl.

The term "aryl$(C_1-C_3)$alkyl" means a radical wherein a one to three carbon alkylene chain is attached to an aryl group, e.g., —CH$_2$CH$_2$-phenyl. Similarly, the term "heteroaryl$(C_1-C_3)$alkyl" means a radical wherein a one to three carbon alkylene chain is attached to a heteroaryl group, e.g., —CH$_2$CH$_2$-pyridyl. The term "substituted aryl$(C_1-C_3)$alkyl" means an aryl$(C_1-C_3)$alkyl radical in which the aryl group is substituted. The term "substituted heteroaryl $(C_1-C_3)$alkyl" means a heteroaryl$(C_1-C_3)$alkyl radical in which the heteroaryl group is substituted. The length of the alkylene chain in the aryl$(C_1-C_3)$alkyl and heteroaryl $(C_1-C_3)$alkyl radicals is preferably one or two carbon atoms. Phenyl, substituted or unsubstituted, is the preferred aryl group in such compounds.

The term "heteroaryl" by itself or as part of another substituent means, unless otherwise stated, an unsubstituted or substituted, stable, mono- or multicyclic heterocyclic aromatic ring system which consists of carbon atoms and from one to four heteroatoms selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

Examples of such heteroaryls include benzimidazolyl, particularly 2-benzimidazolyl; benzofuryl, particularly 3-, 4-, 5-, 6- and 7-benzofuryl; 2-benzothiazolyl and 5-benzothiazolyl; benzothienyl, particularly 3-, 4-, 5-, 6-, and 7-benzothienyl; 4-(2-benzyloxazolyl); furyl; isoquinolyl, particularly 1- and 5-isoquinolyl; isoxazolyl, particularly 3-, 4- and 5-isoxazolyl; imidazolyl, particularly 2-, -4 and 5-imidazolyl; indolyl, particularly 3-, 4-, 5-, 6- and 7-indolyl; oxazolyl; purinyl; pyrrolyl, particularly 2-pyrrolyl and 3-pyrrolyl; pyrazolyl, particularly 3- and 5-pyrazolyl; pyrazinyl; pyridazinyl, particularly 3- and 4-pyridazinyl; pyridyl; pyrimidinyl, particularly 2- and 4-pyrimidinyl; quinoxalinyl, particularly 2- and 5-quinoxalinyl; quinolinyl, particularly 2- and 3-quinolinyl; 5-tetrazolyl; thiazolyl; thienyl; and 3-(1,2,4-triazolyl). The aforementioned listing of heteroaryl moieties is intended to be representative, not limiting.

The term "substituted" means that an atom or group of atoms has replaced hydrogen as the substituent attached to another group. For aryl and heteroaryl groups, "substituted" means any level of substitution, namely mono-, di-, tri-, tetra-, or penta-substitution. The substituents are independently selected. Particularly preferred substituents include halogen; $(C_1-C_8)$alkyl, preferably $(C_1-C_3)$alkyl, most preferably methyl and ethyl; $(C_1-C_8)$alkoxy, preferably $(C_1-C_3)$ alkoxy, most preferably methoxy and ethoxy; and combinations thereof.

The term "subject" or "individual" includes human beings and non-human animals.

By "effective amount" of a compound according to the present invention is meant an amount of compound effective to bring about the indicated biological effect in the treated subject.

DETAILED DESCRIPTION OF THE INVENTION

Figure 1A:
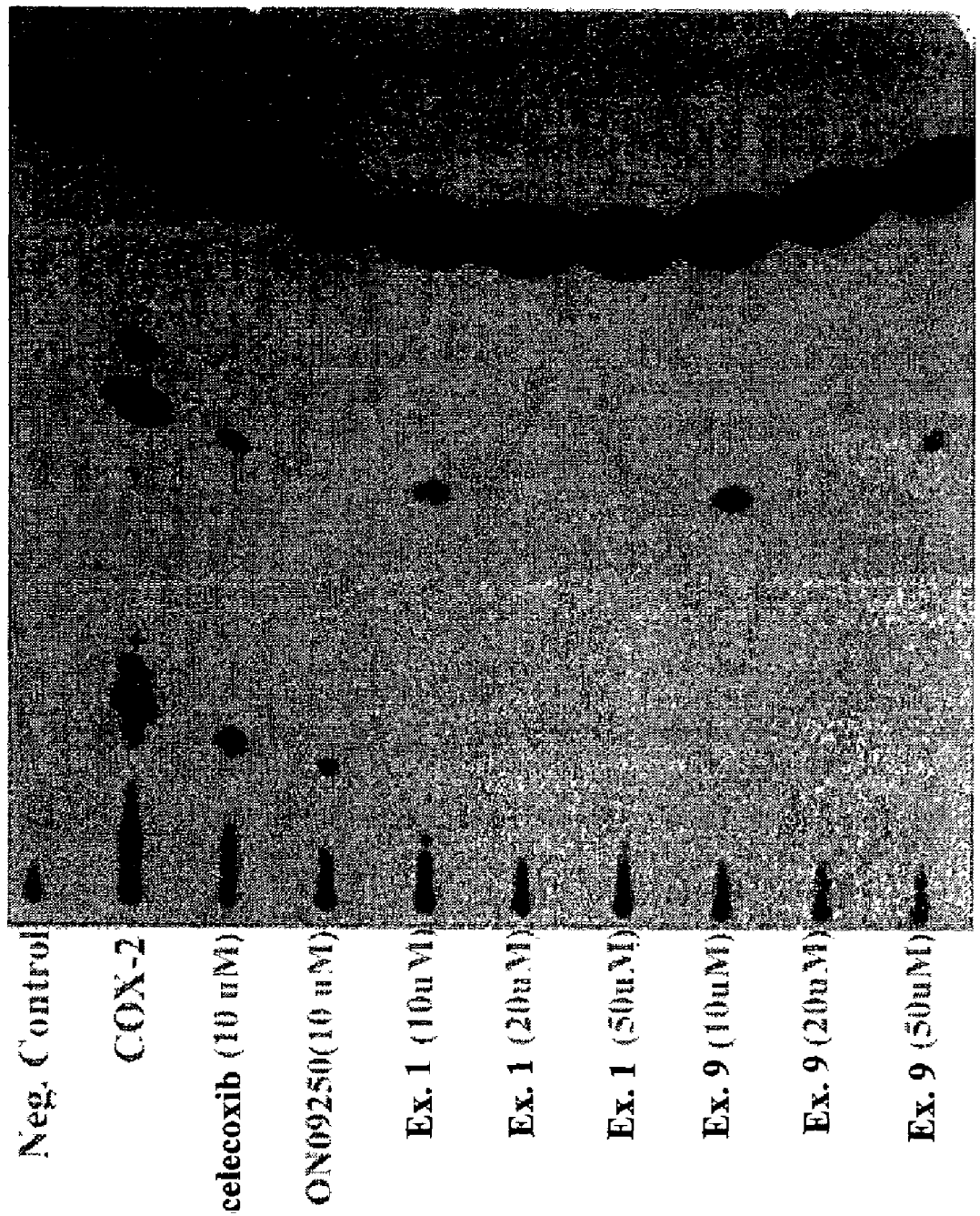
FIGS. 1A and 1B show the results of a thin layer chromatography assay of cyclooxygenase-2 inhibitor activity using [$^{14}$C] arachidonic acid as a substrate. The inhibitory activity of the compounds of Example 1 (4-methyl-benzaldehyde-4-sulfamylphenylhydrazone), Example 2 (4-fluorobenzaldehyde-4-sulfamyl-phenylhydrazone), Example 3 (4-chlorobenzaldehyde-4-sulfamyl-phenylhydrazone), Example 4 (4-bromobenzaldehyde-4-sulfamylphenyl-hydrazone) and Example 9 (4-methoxybenzaldehyde-4-sulfamylphenyl-hydrazone) were compared to the activity of the experimental COX-2 inhibitor ON09250 and the COX-2 inhibitor celecoxib. Lanes marked "Neg. control" contained no COX-2, and no drug. Lanes marked "Cox-2 control" or "COX-2" contained COX-2, but no drug.

The compounds of formula I and Ia are inhibitors of COX-2. COX-2 activity is demonstrated by a cell-free assay in which human recombinant COX-2 is incubated with test compound and [$^{14}$C]-arachidonic acid. The resulting radiolabeled prostanoid compounds, i.e., the products of COX-2 reaction with arachidonic acid, are visualized and/or quantified.

The compounds of the invention may be prepared as in Scheme 1, below. A solution of reactant A in a suitable solvent is added the aryl hydrazine hydrochloride B, and the solution is refluxed. Any solvent suitable for dissolving reactant A may be utilized. The solvent may be nonpolar such as toluene or benzene, or polar such as an alcohol, e.g., ethanol, or an alkyl acetate, e.g. ethyl acetate. The desired condensation product is obtained by isolating the same from the reaction mixture, for example, by evaporating the solvent, such as in a rotoevaporator to obtain a solid. Alternatively, the product is isolated from the reaction mixture by precipitation, such as by pouring the reaction mixture into water to precipitate the product. The precipitated material is filtered and recrystalized, for example from methanol, to provide the desired compound according to formula I.

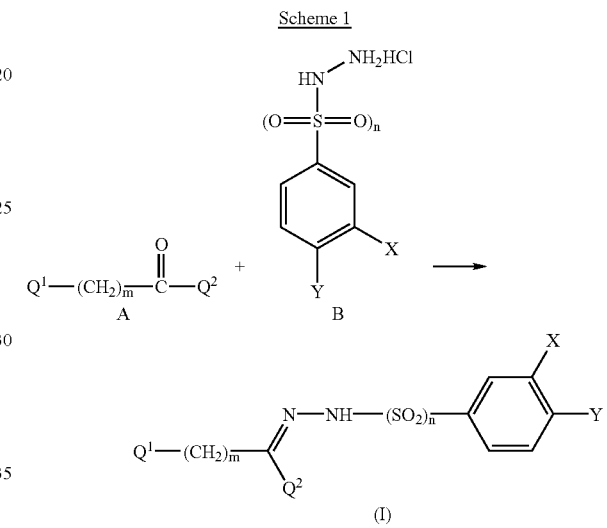

Scheme 1

In one embodiment of the invention, Y is sulfamyl, and the optionally 3-substituted (with hydroxymethyl) 4-sulfamylphenyl hydrazine hydrochloride intermediate B may be obtained from sulfanilamide as follows. A cold stirred mixture of sulfanilamide (34.2 g, 0.2 mol), hydrochloric acid (100 mL) and crushed ice (200 g) is diazotized by dropwise addition of sodium nitrite (14 g, 0.2 mol) in water (25 mL) over 30 minutes. The cold diazonium salt thus formed is rapidly added to a well-cooled solution of stannous chloride (100 g) in hydrochloric acid (150 mL) with vigorous stirring, and the resulting mixture is left in a refrigerator overnight. The precipitated 4-sulfamylphenyl hydrazine hydrochloride is collected at pump and dried. The resulting white crystals of 4-sulfamylphenyl hydrazine hydrochloride have a melting point of 218–220° C.

The compounds of the invention are preferably characterized by a selectivity ratio for COX-2 inhibition over COX-1 inhibition of at least about 20, more preferably at least about 30, even more preferably at least about 50, and most preferably at least about 100. COX inhibition may be determined in vitro by enzyme assays well-known to those skilled in the art, such as the enzyme assay method described later herein.

The compounds of the present invention may take the form or pharmaceutically acceptable salts. The term "pharmaceutically acceptable salts", embraces salts commonly used to form alkali metal salts and to form addition salts of free acids or free bases. Where reference is made to "compound of formula I" or "compounds of formula Ia" or a "compound of the invention", it is understood that pharmaceutically acceptable salts are also included. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, alginic, beta-hydroxybutyric, salicylic, galactaric and galacturonic acid. Suitable pharmaceutically acceptable base addition salts of compounds of formula I include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I or Ia by reacting, for example, the appropriate acid or base with the compound of formula I or Ia.

The compounds of the present invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and not deleterious to the recipient.

The compounds of the invention may be administered to individuals (animals, most particularly mammals including humans) afflicted with any disorder characterized by undesirable prostaglandin production resulting from cyclooxygenase activity, particularly COX-2. activity ("cyclooxygenase-mediated disorder"). In particular, the compounds of the invention are believed useful in treating inflammation and inflammation-related disorders, by administering to a subject having or susceptible to such inflammation or inflammation-related disorder and effective amount of a compound according to formula I or Ia. Inflammation is associated with a variety of disease conditions. For a list of such disease conditions treatable by cyclooxygenase inhibitors, and COX-2 inhibitors in particular, see U.S. Pat. Nos. 5,604,253 and 5,908,852, the entire disclosures of which are incorporated herein by reference. Such conditions include, for example, arthritis, including but not limited to rheumatoid arthritis, spondyloarthropathies, gouty arthritis, osteoarthritis, systemic lupus erythematosus and juvenile arthritis. Such conditions further include rheumatic fever, symptoms associated with influenza or other viral infections, common cold, low back and neck pain, dysmenorrhea, headache, toothache, sprains and strains, myositis, neuralgia, synovitis, gout and ankylosing spondylitis, bursitis, and following surgical and dental procedures. The compounds of the invention are believed useful as analgesics for treating or alleviating all forms of pain. The compounds are believed useful in the treatment of other disorders including asthma, bronchitis, tendonitis, bursitis; skin related conditions such as psoriasis, eczema, burns and dermatitis; gastrointestinal conditions such as inflammatory bowel disease, Crohn's disease, gastritis, irritable bowel syndrome and ulcerative colitis and for the prevention of colorectal cancer; the treatment of inflammation in such diseases as vascular diseases, migraine headaches, periarteritis nodosa, thyroiditis, aplastic anemia, Hodgkin's disease, sclerodoma, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds of the invention are believed useful as antipyretics for the treatment of fever.

In addition, compounds of the invention may inhibit cellular neoplastic transformations and metastatic tumor growth and hence can be used in the treatment of cancer. In particular, the present invention provides a method for treating or preventing a neoplasia that produces a prostaglandin in a subject in need of such treatment or prevention, the method comprises treating the subject with a therapeutically effective amount of a compound of formula I or Ia. The term "neoplasia" includes neoplasias that produce prostaglandins or express a cyclooxygenase, including both benign and cancerous tumors, growths and polyps. Neoplasias believed treatable with cyclooxygenase inhibitors are discussed in U.S. Pat. No. 5,972,986, the entire disclosure of which is incorporated herein by reference. The compounds may be used to inhibit the growth or an established neoplasm, i.e., to induce regression, or to prevent or delay the onset of the neoplasm.

According to U.S. Pat. No. 5,972,986, neoplasias that produce prostaglandins, and which are therefore believed treatable with the compounds of the invention, include brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

The compounds of the invention may also be useful in the treatment of angiogenesis-mediated disorders. Thus, a method for treating, inhibiting or delaying the onset of an angiogenesis-mediated disorder in a subject is provided comprising administering to a subject in need of such treatment an effective amount of a compound according to the present invention. Angiogenesis-mediated disorders which may be treatable with cyclooxygenase inhibitors are discussed in U.S. Pat. No. 6,025,353, the entire disclosure of which is incorporated herein by reference. According to U.S. Pat. No. 6,025,353, such disorders include, for example, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

The compounds of the invention may also be useful in the treatment of Alzheimer's Disease, presenile dementia, stroke and cerebral ischemia. Thus, a method for treating, inhibiting or delaying the onset of Alzheimer's Disease, presenile dementia, stroke or cerebral ischemia in a subject is provided comprising administering to a subject in need of such treatment an effective amount of a compound according to the present invention. U.S. Pat. Nos. 6,486,194, 5,932,598 and 6,432,999, the entire disclosures of which are incorporated herein by reference, disclose that neurodegenerative diseases, including Alzheimer's disease, stroke and cerebral ischemia may be treated by administering non-steroidal cyclooxygenase-2 inhibitors.

The compounds of the invention may also be useful in the treatment of tissue ischemia, such as ischemia of the myocardium. Thus, a method for treating, inhibiting or delaying the onset of tissue ischemia, particularly stroke (CNS ischemia), and ischemia of the myocardium in a subject is provided comprising administering to a subject in need of such treatment an effective amount of a compound according to the present invention. U.S. Pat. Nos. 6,451,794, 6,432,999 and 5,932,598, the entire disclosures of which are incorporated herein by reference, disclose that tissue damage associated with tissue ischemia, such as ischemia of the myocardium, may be treated by administration of compounds that are selective inhibitors of COX-2.

The compounds may be administered by any route, including oral and parenteral administration. Parenteral administration includes, for example, intravenous, intramuscular, intraarterial, intraperitoneal, intranasal, rectal, or subcutaneous administration. The active agent is preferably administered with a pharmaceutically acceptable carrier selected on the basis of the selected route of administration and standard pharmaceutical practice.

The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol.

For oral administration, the active agent may be combined with one or more solid inactive ingredients for the preparation of tablets, capsules, or other suitable oral dosage forms. For example, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.01 to about 150 mg/kg/day may be utilized. Higher or lower doses are also contemplated.

The practice of the invention is illustrated by the following non-limiting examples. Each synthesis is carried out according to the General Procedure. The compounds in Table 1 are thus prepared.

General Procedure

To a solution of aryl aldehyde or ketone (5 mmol) in ethanol (50 mL) is added aryl hydrazine hydrochloride (6 mmol) and the solution is refluxed for 90 minutes. The reaction mixture is cooled and poured in to cold water (100 mL). The precipitated material is filtered and recrystalized from methanol.

TABLE 1

$$Q^{1a}\underset{Q^2}{\overset{}{C}}=N-\underset{H}{N}-(SO_2)_n-\underset{}{\overset{X}{\bigcirc}}-Y$$

| Ex. | $Q^{1a}$ | Y | $Q^2$ | n | X | MP (° C.) |
|---|---|---|---|---|---|---|
| 1 | 4-$CH_3C_6H_4$ | $SO_2NH_2$ | H | 0 | H | 216–218 |
| 2 | 4-$FC_6H_4$ | $SO_2NH_2$ | H | 0 | H | 205–206 |
| 3 | 4-$ClC_6H_4$ | $SO_2NH_2$ | H | 0 | H | 181–182 |
| 4 | 4-$BrC_6H_4$ | $SO_2NH_2$ | H | 0 | H | 190–192 |
| 5 | 3-Indoyl | $SO_2NH_2$ | H | 0 | H | 265–269 |
| 6 | $C_6H_5CH_2$ | $SO_2NH_2$ | $CF_3$ | 0 | H | 114–118 |
| 7 | $C_6H_5CH_2$ | H | $CF_3$ | 1 | H | 133–134 |
| 8 | $C_6H_5CH_2$ | $CH_3$ | $CF_3$ | 1 | H | 135–137 |
| 9 | 4-$CH_3OC_6H_4$ | $SO_2NH_2$ | H | 0 | H | 228–231 |
| 10 | 2,4-$Cl_2C_6H_3$ | $SO_2NH_2$ | H | 0 | H | 219–221 |
| 11 | 4-$BrC_6H_4$ | $SO_2NH_2$ | $CH_3$ | 0 | H | — |
| 12 | 4-$ClC_6H_4$ | $SO_2CH_3$ | H | 0 | H | — |
| 13 | Furan | $SO_2CH_3$ | H | 0 | H | — |
| 14 | Thiophene | $SO_2NH_2$ | $CH_3$ | 0 | H | — |

EXAMPLE 1

4-Methylbenzaldehyde-4-sulfamylphenylhydrazone

A solution of 4-methylbenzaldehyde (5 mmol) and 4-sulfamyl-phenylhydrazine hydrochloride was subjected to the General Procedure. The title compound, melting point 216–218° C., was obtained in 45% yield.

EXAMPLE 2

4-Fluorobenzaldehyde-4-sulfamylphenylhydrazone

A solution of 4-fluorobenzaldehyde (5 mmol) and 4-sulfamyl-phenylhydrazine hydrochloride was subjected to the General Procedure. The title compound, melting point 205–206° C., was obtained in 58% yield.

EXAMPLE 3

4-Chlorobenzaldehyde-4-sulfamylphenylhydrazone

A solution of 4-chlorobenzaldehyde (5 mmol) and 4-sulfamylphenylhydrazine hydrochloride was subjected to the General Procedure. The title compound, melting point 181–182° C., was obtained in 60% yield.

EXAMPLE 4

4-Bromobenzaldehyde-4-sulfamylphenylhydrazone

A solution of 4-bromobenzaldehyde (5 mmol) and 4-sulfamylphenyl-hydrazine hydrochloride was subjected to the General Procedure. The title compound, melting point 190–192° C., was obtained in 66% yield.

EXAMPLE 5

Indolecarboxaldehyde-4-sulfamylphenylhydrazone

A solution of 3-indolecarboxaldehyde (5 mmol) and 4-sulfamylphenyl-hydrazine hydrochloride was subjected to the General Procedure. The title compound, melting point 265–269° C., was obtained in 50% yield.

EXAMPLE 6

Benzyl trifluoromethylketone-4-sulfamylphenylhydrazone

A solution of benzyl trifluoromethylketone (5 mmol) and 4-sulfamylphenyl-hydrazine hydrochloride was subjected to the General Procedure. The title compound, melting point 114–118° C., was obtained in 76% yield.

EXAMPLE 7

Benzyl trifluoromethylketone benzenesulfonylhydrazone

A solution of benzyl trifluoromethylketone (5 mmol) and benzene sulfonylhydrazide hydrochloride was subjected to the General Procedure. The title compound, melting point 133–134° C., was obtained in 75% yield.

EXAMPLE 8

Benzyl trifluoromethylketone toluenesulfonylhydrazone

A solution of benzyl trifluoromethylketone (5 mmol) and toluene sulfonylhydrazide hydrochloride was subjected to the General Procedure. The title compound, melting point 135–137° C., was obtained in 76% yield.

EXAMPLE 9

4-Methoxybenzaldehyde-4-sulfamylphenylhydrazone

A solution of 4-methoxybenzaldehyde (5 mmol) and 4-sulfamylphenyl-hydrazine hydrochloride was to the General Procedure. The title compound, melting point 228–231° C., was obtained in 62% yield.

EXAMPLE 10

2,4-Dichlorobenzaldehyde-4-sulfamylphenylhydrazone

A solution of 2,4-dichlorobenzaldehyde (5 mmol) and 4-sulfamylphenylhydrazine hydrochloride was subjected to the General Procedure. The title compound, melting point 219–221° C., was obtained in 59% yield.

EXAMPLE 11

4-Bromoacetophenone-4-sulfamylphenylhydrazone

A solution of 4-bromoacetophenone (5 mmol) and 4-sulfamylphenylhydrazine hydrochloride is subjected to the General Procedure. The title compound is isolated as described in the general procedure.

EXAMPLE 12

4-Chlorobenzaldehyde-4-sulfamylphenylhydrazone

A solution of 4-chlorobenzaldehyde (5 mmol) and 4-sulfamylphenylhydrazine hydrochloride is subjected to the General Procedure. The title compound is isolated as described in the general procedure.

EXAMPLE 13

2-Furancarboxaldehyde-4-sulfamylphenylhydrazone

A solution of 2-furancarboxaldehyde (5 mmol) and 4-sulfamylphenylhydrazine hydrochloride is subjected to the General Procedure. The title compound is isolated as described in the general procedure.

EXAMPLE 14

2-acetylthiophene-4-sulfamylphenylhydrazone

A solution of 2-acetylthiophene (5 mmol) and 4-sulfamylphenylhydrazine hydrochloride is subjected to the General Procedure. The title compound is isolated as described in the general procedure.

Cyclooxygenase Enzyme Assay

Figure 1B:
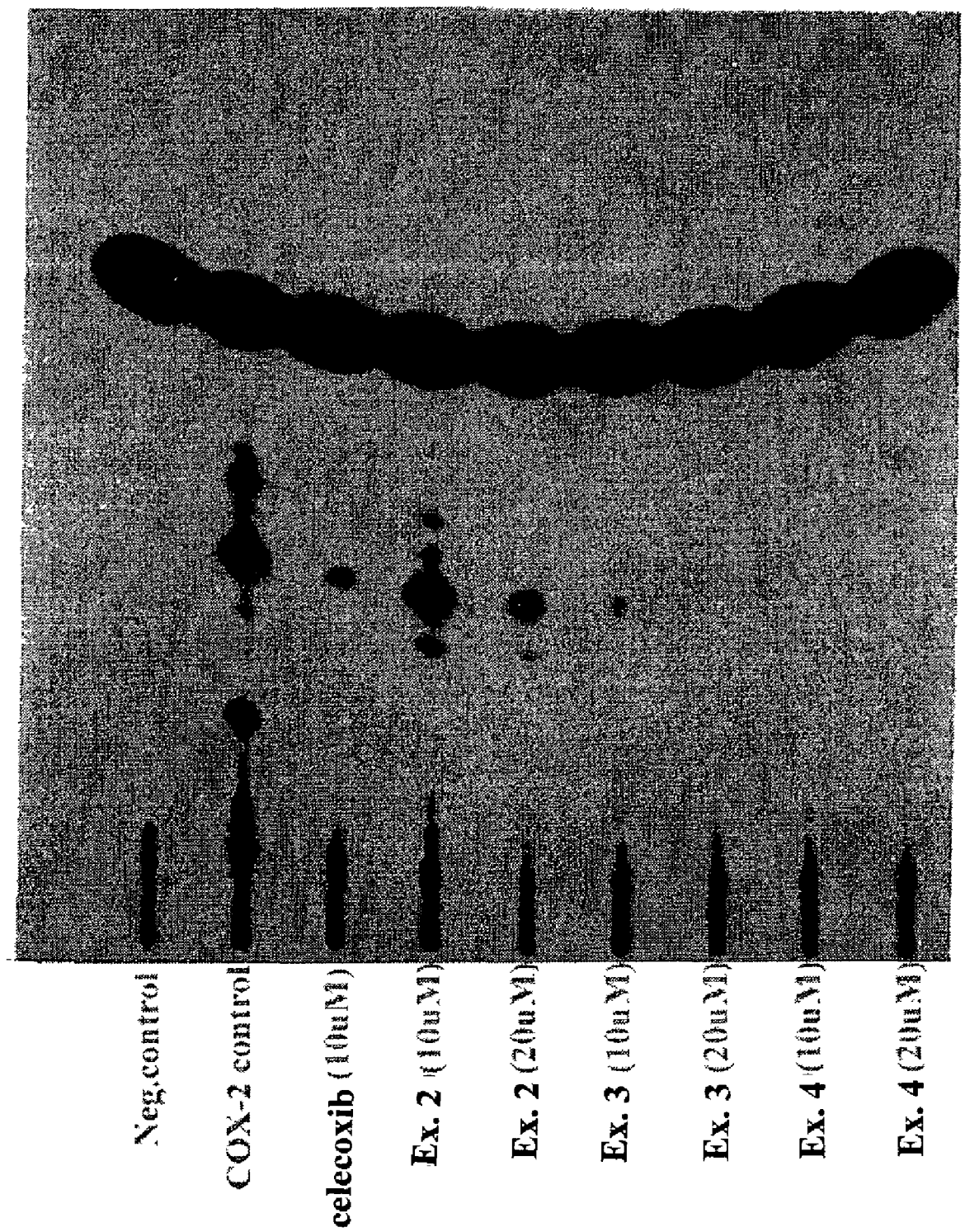

The compounds of Examples 1, 2, 3, 4 and 9 were tested for inhibitory activity against COX-2. Cyclooxygenase activity of COX-2 (Oxford Biomedical Research Inc.) was assayed by a thin layer chromatography (TLC) method using [$^{14}$C] arachidonic acid as a substrate. All inhibitors were dissolved in dimethyl sulfoxide (DMSO) to a stock solution of 5 mM. Two positive controls were dissolved in DMSO in the same manner, the experimental COX-2 inhibitor ON09250 and the COX-2 inhibitor celecoxib. Human recombinant COX-2 (3 units) was incubated with inhibitors at several concentrations in a solution containing 10 mM Tris-HCl, pH 7.8, 500 µM phenol and hematin for 90 to 120 minutes at room temperature (24° C.). In a negative control (no drug, no COX-2) and COX-2 control (no drug, with COX-2), equal volumes of DMSO without drug were added to the incubation mixture. After incubation for 90–120 minutes, [1-$^{14}$C] arachidonic acid (50 µM, 51 mCi/mmol) (DuPont NEN) was added and incubated at 37° C. for 2 minutes. The reaction was terminated by extraction with 1 mL of ethyl acetate. The ethyl acetate layer was transferred into a fresh tube and evaporated to dryness in a Speedvac vacuum dryer. The contents of the tubes were reconstituted in 20 mL of ethyl acetate and spotted on a TLC plate (J. T. Baker, Phillipsburg, N.J.) and developed in a mobile phase containing chloroform/methanol (95:5) at 4° C. The results are shown in FIGS. 1A and 1B.

Soft Agar Assay

The Example 2, 3, 4 and 9 compounds were compared to the COX-2 inhibitor celecoxib in inhibiting the growth of DLD-1 cells in soft agar. DLD-1 cells are human colorectal carcinoma cells that overexpress COX-2. DLD-1 cells grow in soft agar and form tumors in nude mice. The soft agar assay was performed as follows. Bottom agar was first prepared as a 3 mL layer of 0.8% noble agar prepared in complete growth medium (DMEM containing 10% FBS and 500 units of penicillin-streptomycin) and placed into 60 mm² tissue culture dishes. The tumor cells were trypsinized from normal growth flasks while in exponential growth. The cells were counted by using a hemacytometer and 5.0×10⁴ viable cells were mixed with 0.4% noble agar containing growth medium and various concentrations of drugs. Non-treated control plates received DMSO alone. Each drug concentration was run in duplicate. The concentration range was normally between 10 μM to 75 μM. The plates were incubated at 37° C. under 95% humidity for three weeks and stained with a 0.05% (w/v) nitroblue tetrazolium solution. This solution will only stain viable cells so that all growing cell in the form of colonies will appear blue. The plates were photographed using an Olympus stereoscope mounted with a SONY digital camera system. The results are shown in Table 2.

TABLE 2

Inhibition of Anchorage-independent Growth of Human Colo-rectal Tumor Cells

| Example | Concentration Required for Complete DLD-1 Colony Growth Inhibition |
|---------|------------------------------------------------------------------|
| 2 | 30 μM |
| 3 | 20 μM |
| 4 | <20 μM |
| 9 | >75 μM |

Table 2 shows that three out of the four hydrazines tested were able to completely inhibit the anchorage-independent growth of human colo-rectal cells at concentrations below 30 μM. The most active compound in this assay system was 4-bromobenzaldehyde-4-sulfamylphenylhydrazone (Ex. 4), which was able to completely inhibit at 20 μM.

In Vitro Cytotoxicity Assay

The human colo-rectal carcinoma cell lines DLD-1, HT29, and HCT116, and the human prostate carcinoma cell line DU145, were grown exponentially and plated onto 6 well dishes at a cell density of 1.0×10⁵ cells per 35 mm well. Various concentration of 4-bromobenzaldehyde-4-sulfamylphenylhydrazone (Ex. 4) or DMSO were added 24 hours later. The number of viable cells was determined at each concentration tested 96 hours later by trypan exclusion using a hemacytometer. The $GI_{50}$ (concentration of drug that inhibits 50% of tumor cell growth when compared to tumor cells treated with same volume of DMSO) was determined for each cell line. The results are shown in Table 3.

TABLE 3

Growth Inhibitory Activity of 4-Bromobenzaldehyde-4-sulfamylphenylhydrazone Against Human Carcinoma Cell Lines

| Cell Line | $GI_{50}$ |
|-----------|-----------|
| DLD-1 | 30 μM |
| HT29 | 8 μM |
| HCT116 | 30 μM |
| DU145 | 30 μM |

Figure 2:
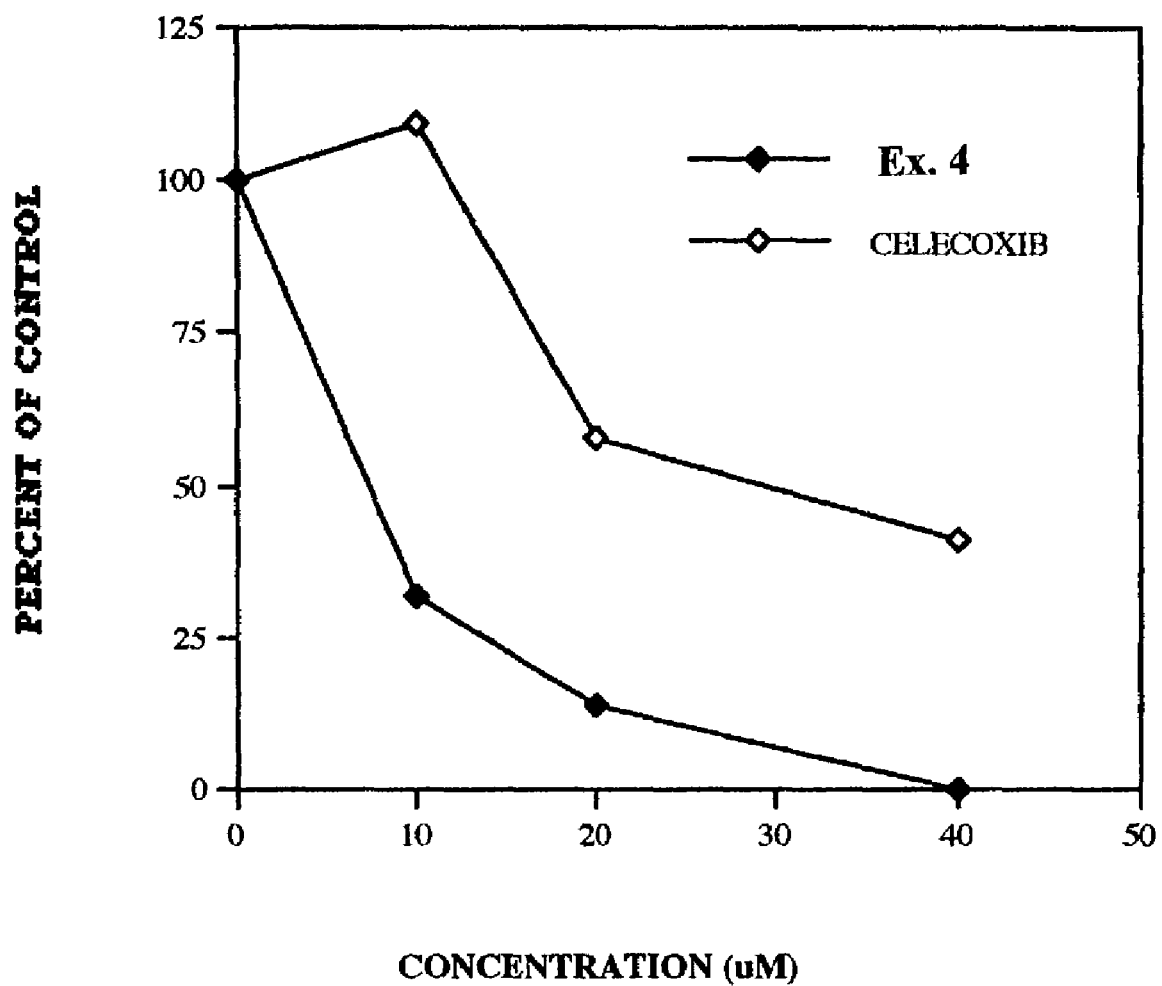
FIG. 2 compares the growth inhibitory activity of the Example 4 compound 4-bromobenzaldehyde-4-sulfamylphenylhydrazone and celecoxib against the human colo-rectal tumor cell line HT29. The data is plotted as the percent of viable cells remaining as compared to non-treated cells.

The same protocol was used to compare the growth inhibitory activity of 4-bromobenzaldehyde-4-sulfamylphenylhydrazone and celecoxib against the human colo-rectal tumor cell line HT29. The results are shown in FIG. 2. The data are plotted as the percent of viable cells remaining as compared to DMSO (non-treated) cells. The data demonstrate that 4-bromobenzaldehyde-4-sulfamylphenylhydrazone ($GI_{50}$=8 μM) has more tumor cell growth inhibitory activity than celecoxib ($GI_{50}$=25 μM).

In vivo Toxicity Assay

The compound of Example 4 was examined for in vivo toxicity in mice. Mice received intraperitoneal doses of compound suspended in DMSO, ranging from 25 to 400 mg/kg. Survival at seven days was determined. The results are shown in Table 4, indicating very low mammalian toxicity:

TABLE 4

Percent Survival of Mice Following Intraperitoneal Administration of 4-Bromobenzaldehyde-4-sulfamylphenylhydrazone

| Dose | 25 mg/kg | 50 mg/kg | 100 mg/kg | 200 mg/kg | 400 mg/kg |
|------|----------|----------|-----------|-----------|-----------|
| Survival | 100% | 100% | 100% | 100% | 80% |

Bioavailability Assay

The bioavailability of compound of Example 4 was examined as follows. Mice received a single dose (25 or 50 mg/kg) of compound suspended in DMSO via intraperitoneal injection. Plasma drug concentration was measured 120 minutes post injection. The results are shown in Table 5, indicating a high level of bioavailability:

TABLE 5

Intraperitoneal Absorption of 4-Bromobenzaldehyde-4-sulfamylphenyl-hydrazone

| Single Dose (mg/kg) | Number of Animals | Plasma Drug Concentration (μg/ml) at 120 min. |
|---------------------|-------------------|-----------------------------------------------|
| 25 | 1 | 38 |
| 50 | 2 | 165 |

All references cited herein are incorporated herein by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A pharmaceutical composition comprising a pharmaceutically acceptable carrier and a compound of formula I

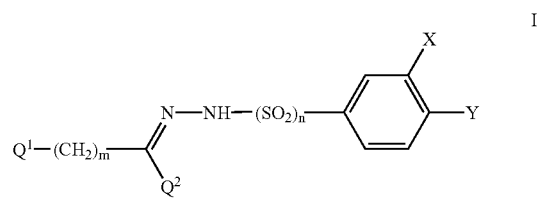

wherein:
Q¹ is selected from the group consisting of hydrogen, trifluoromethyl, $(C_1–C_8)$alkyl, substituted and unsubstituted aryl, and substituted and unsubstituted heteroaryl;
Q² is selected from the group consisting of hydrogen, trifluoromethyl, $(C_1–C_8)$alkyl, substituted and unsubstituted aryl, substituted and unsubstituted heteroaryl, substituted and unsubstituted aryl($C_1$–$C_3$)alkyl, and substituted and unsubstituted heteroaryl($C_1$–$C_3$)alkyl;

n is zero or one;

m is zero, one, two or three;

X is selected from the group consisting of hydrogen and hydroxymethyl; and

Y is selected from the group consisting of hydrogen, ($C_1$–$C_8$)alkyl, ($C_1$$C_8$)alkoxy, nitro, amino, sulfamyl and ($C_1$–$C_3$)alkylsulfonyl;

provided:
(i) $Q^1$ and $Q^2$ may not both be hydrogen in the same compound;
(ii) $Q^1$ and $Q^2$ may not both be ($C_1$–$C_8$)alkyl in the same compound;
(iii) when n is zero, Y must be sulfamyl or ($C_1$–$C_3$)alkylsulfonyl;
(iv) when m and n are both zero and $Q^2$ is —H or ($C_1$–$C_8$)alkyl, then $Q^1$ may not be phenyl, unless substituted at the 4-position by other than hydroxy, alkyl, alkoxy or alkoxyalkyl; and
(v) when n is one, $Q^2$ must be trifluoromethyl; or a pharmaceutically acceptable salt thereof.

2. The composition according to claim 1 wherein:

$Q^1$ is selected from the group consisting of hydrogen, trifluoromethyl, ($C_1$–$C_8$)alkyl, substituted and unsubstituted aryl, and substituted and unsubstituted heteroaryl;

$Q^2$ is selected from the group consisting of hydrogen, trifluoromethyl, ($C_1$–$C_8$)alkyl, substituted and unsubstituted aryl, substituted and unsubstituted heteroaryl, substituted and unsubstituted aryl($C_1$–$C_3$)alkyl, and substituted and unsubstituted heteroaryl($C_1$–$C_3$)alkyl; and wherein the substituents for the substituted aryl, substituted heteroaryl, substituted aryl($C_1$–$C_3$)alkyl, and substituted heteroaryl($C_1$–$C_3$)alkyl comprising $Q^1$ or $Q^2$ are independently selected from the group consisting of halogen, ($C_1$–$C_8$)alkyl, ($C_1$–$C_8$)alkoxy, nitro, cyano, carboxy, carboxy($C_1$–$C_3$)alkoxy, hydroxy, ($C_2$–$C_6$)hydroxyalkyl, phosphonato, amino, ($C_1$–$C_8$)acylamino, sulfamyl, acetoxy, di($C_1$–$C_6$)alkylamino($C_2$–$C_6$) alkoxy), trifluoromethyl and

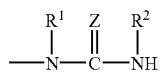

wherein:

Z is oxygen or sulfur, $R^1$ is selected from the group consisting of hydrogen, ($C_1$–$C_8$)alkyl, ($C_2$–$C_8$)heteroalkyl, substituted phenyl and unsubstituted phenyl, and $R^2$ is selected from the group consisting of hydrogen, ($C_1$–$C_8$)alkyl, ($C_2$–$C_8$)heteroalkyl, substituted aryl, unsubstituted aryl, substituted heteroaryl, unsubstituted heteroaryl, substituted aryl($C_1$–$C_3$)alkyl, unsubstituted aryl($C_1$–$C_3$)alkyl and ($C_1$–$C_6$)alkoxycarbonyl($C_1$–$C_6$)alkylenyl; and wherein the substituents for the substituted aryl and substituted heteroaryl groups comprising or included within $R^1$ and $R^2$, are independently selected from the group consisting of halogen, ($C_1$–$C_8$)alkyl, ($C_1$–$C_8$) alkoxy, nitro, cyano, carboxy, carboxy($C_1$–$C_3$)alkoxy, hydroxy, hydroxy($C_2$–$C_6$)alkyl, phosphonato, amino, ($C_1$–$C_8$)acylamino, sulfamyl, acetoxy, di($C_1$–$C_6$)alkylamino($C_2$–$C_6$ alkoxy) and trifluoromethyl.

3. The composition according to claim 2 wherein n is zero, and Y is sulfamyl or ($C_1$–$C_3$)alkylsulfonyl.

4. The composition according to claim 3 wherein $Q^2$ is selected from the group consisting of hydrogen, ($C_1$–$C_8$) alkyl and trifluoromethyl.

5. The composition according to claim 4 wherein X is hydrogen.

6. The composition according to claim 5 wherein $Q^1$ is substituted or unsubstituted phenyl.

7. The composition according to claim 6 wherein $Q^1$ is substituted phenyl, and the substituents are selected from the group consisting of halogen, ($C_1$–$C_8$)alkyl, ($C_1$–$C_8$)alkoxy or combination thereof.

8. The composition according to claim 7 wherein $Q^1$ is 2,4-di-substituted phenyl.

9. The composition according to claim 8 wherein m is zero and $Q^2$ is hydrogen.

10. The composition according to claim 7 wherein $Q^1$ is 4-monosubstituted phenyl.

11. The composition according to claim 10 wherein m is zero and $Q^2$ is hydrogen.

12. The composition according to claim 2 wherein m is one, and $Q^2$ is trifluoromethyl.

13. The composition according to claim 12 wherein Y is selected from the group consisting of hydrogen, ($C_1$–$C_8$) alkyl, sulfamyl and ($C_1$–$C_3$)alkylsulfonyl.

14. The composition according to claim 13 wherein Y is hydrogen or ($C_1$–$C_8$)alkyl.

15. The compound according to claim 12 which is benzyl trifluoromethylketone-4-sulfamylphenylhydrazone, or a pharmaceutically acceptable salt thereof.

16. A pharmaceutical composition comprising a pharmaceutically acceptable carrier and a compound of formula Ia

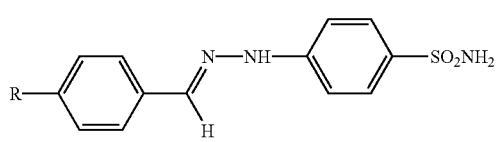

wherein,

R is selected from the group consisting of halogen, ($C_1$–$C_8$)alkyl and ($C_1$–$C_8$)alkoxy; or a pharmaceutically acceptable salt thereof.

17. The composition according to claim 16 wherein the compound is 4-fluorobenzaldehyde-4-sulfamylphenylhydrazone, or a pharmaceutically acceptable salt thereof.

18. The composition according to claim 16 wherein the compound is 4-chlorobenzaldehyde-4-sulfamylphenylhydrazone, or a pharmaceutically acceptable salt thereof.

19. The composition according to claim 16 wherein the compound is 4-bromobenzaldehyde-4-sulfamylphenylhydrazone, or a pharmaceutically acceptable salt thereof.

20. The composition according to claim 16 wherein the compound is 4-methoxybenzaldehyde-4-sulfamylphenylhydrazone, or a pharmaceutically acceptable salt thereof.

21. The composition according to claim 16 wherein the compound is 4-methylbenzaldehyde-4-sulfamylphenylhydrazone, or a pharmaceutically acceptable salt thereof.

22. A compound of formula I

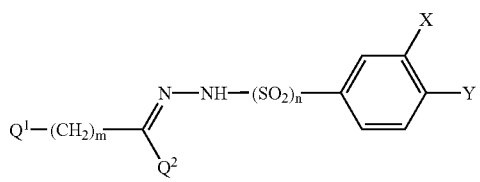

wherein:

$Q^1$ is selected from the group consisting of hydrogen, trifluoromethyl, $(C_1-C_8)$alkyl, substituted and unsubstituted aryl, and substituted and unsubstituted heteroaryl;

$Q^2$ is selected from the group consisting of hydrogen, trifluoromethyl, $(C_1-C_8)$alkyl, substituted and unsubstituted aryl, substituted and unsubstituted heteroaryl, substituted and unsubstituted aryl$(C_1-C_3)$alkyl, and substituted and unsubstituted heteroaryl$(C_1-C_3)$alkyl;

n is zero or one;

m is zero, one, two or three;

X is selected from the group consisting of hydrogen and hydroxymethyl; and

Y is selected from the group consisting of hydrogen, $(C_1-C_8)$alkyl, $(C_1-C_8)$alkoxy, nitro, amino, sulfamyl and $(C_1-C_3)$alkylsulfonyl;

provided:
(i) $Q^1$ and $Q^2$ may not both be hydrogen in the same compound;
(ii) $Q^1$ and $Q^2$ may not both be $(C_1-C_8)$alkyl in the same compound;
(iii) when n is zero, Y must be sulfamyl or $(C_1-C_3)$alkylsulfonyl;
(iv) when m and n are both zero and $Q^2$ is —H or $(C_1-C_8)$alkyl, then $Q^1$ may not be phenyl, unless substituted at the 4-position by other than chlorine, bromine, hydroxy, alkyl, alkoxy or alkoxyalkyl; and
(v) when n is one, $Q^2$ must be trifluoromethyl;

or a pharmaceutically acceptable salt thereof.

23. The compound according to claim 22 wherein the compound is benzyl trifluoromethyl-ketone-4-sulfamylphenylhydrazone or a pharmaceutically acceptable salt thereof.

24. A compound of formula Ia

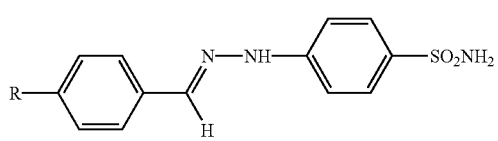

wherein,

R is selected from the group consisting of fluorine, $(C_1-C_8)$alkyl and $(C_2-C_8)$alkoxy; or a pharmaceutically acceptable salt thereof.

25. The compound according to claim 24 wherein the compound is 4-fluorobenzaldehyde-4-sulfamylphenylhydrazone, or a pharmaceutically acceptable salt thereof.

26. The compound according to claim 24 wherein R is selected from the group consisting of $(C_1-C_8)$alkyl and $(C_2-C_8)$alkoxy.

27. The compound according to claim 26 which is 4-methylbenzaldehyde-4-sulfamylphenylhydrazone, or a pharmaceutically acceptable salt thereof.

28. A process for preparing a compound according to claim 22 of the formula I

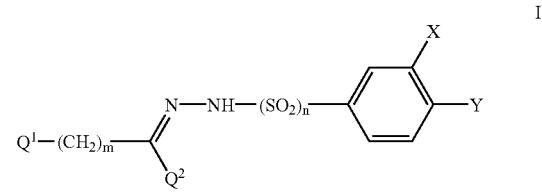

wherein:

$Q^1$ is selected from the group consisting of hydrogen, trifluoromethyl, $(C_1-C_8)$alkyl, substituted and unsubstituted aryl, and substituted and unsubstituted heteroaryl;

$Q^2$ is selected from the group consisting of hydrogen, trifluoromethyl, $(C_1-C_8)$alkyl, substituted and unsubstituted aryl, substituted and unsubstituted heteroaryl, substituted and unsubstituted aryl$(C_1-C_3)$alkyl, and substituted and unsubstituted heteroaryl$(C_1-C_3)$alkyl;

n is zero or one;

m is zero, one, two or three;

X is selected from the group consisting of hydrogen and hydroxymethyl; and

Y is selected from the group consisting of hydrogen, $(C_1-C_8)$alkyl, $(C_1-C_8)$alkoxy, nitro, amino, sulfamyl and $(C_1-C_3)$alkylsulfonyl;

provided:
(i) $Q^1$ and $Q^2$ may not both be hydrogen in the same compound;
(ii) $Q^1$ and $Q^2$ may not both be $(C_1-C_8)$alkyl in the same compound;
(iii) when n is zero, Y must be sulfamyl or $(C_1-C_3)$alkylsulfonyl;
(iv) when m and n are both zero and $Q^2$ is —H or $(C_1-C_8)$alkyl, then $Q^1$ may not be phenyl, unless substituted at the 4-position by other than chlorine, bromine, hydroxy, alkyl, alkoxy or alkoxyalkyl; and
(v) when n is one, $Q^2$ must be trifluoromethyl;

the process comprising reacting a compound of formula II;

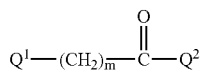

with a compound of formula III,

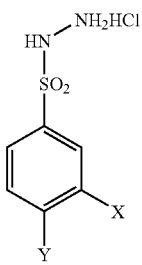

obtaining a compound of claim 22, or a pharmaceutically acceptable salt thereof.

29. A process according to claim 28 wherein Y is sulfamyl.

30. A process for preparing a compound according to claim 24 of the formula Ia

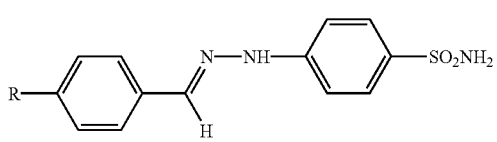

R is selected from the group consisting of fluorine, $(C_1–C_8)$alkyl and $(C_2–C_8)$alkoxy;

the process comprising reacting a compound of formula IIa;

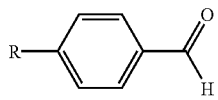

with a compound of formula IIIa,

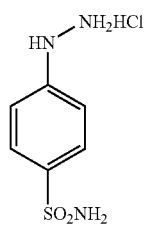

and obtaining a compound of claim 24, or a pharmaceutically acceptable salt thereof.

31. A method for treating a cyclooxygenase-mediated disorder comprising administering to a patient in need of such treatment an effective amount of a composition according to claim 1.

32. A method for treating a cyclooxygenase-mediated disorder comprising administering to a patient in need of such treatment an effective amount of a composition according to claim 16.

33. A method for treating inflammation or an inflammation-mediated disorder comprising administering to a subject in need of such treatment an effective amount of a composition according to claim 1.

34. A method for treating inflammation or an inflammation-mediated disorder comprising administering to a subject in need of such treatment an effective amount of a composition according to claim 16.

35. A method for treating a neoplasia comprising administering to a subject in need of such treatment an effective amount of a composition according to claim 1.

36. A method for treating a neoplasia comprising administering to a subject in need of such treatment an effective amount of a composition according to claim 16.

37. A method for treating an angiogenesis-mediated disorder, comprising administering to a subject in need of such treatment an effective amount of a composition according to claim 1.

38. A method for treating an angiogenesis-mediated disorder, comprising administering to a subject in need of such treatment an effective amount of a composition according to claim 16.

39. A method for treating Alzheimer's Disease, comprising administering to a subject in need of such treatment an effective amount of a composition according to claim 1.

40. A method for treating Alzheimer's Disease, comprising administering to a subject in need of such treatment an effective amount of a composition according to claim 16.

41. A method for treating stroke, comprising administering to a subject in need of such treatment an effective amount of a composition according to claim 1.

42. A method for treating stroke, comprising administering to a subject in need of such treatment an effective amount of a composition according to claim 16.

43. A method for treating myocardial ischemia, comprising administering to a subject in need of such treatment an effective amount of a composition according to claim 1.

44. A method for treating myocardial ischemia, comprising administering to a subject in need of such treatment an effective amount of a composition according to claim 16.

* * * * *